US009523131B2

(12) United States Patent (10) Patent No.: US 9,523,131 B2
Brillowska-Dabrowska (45) Date of Patent: Dec. 20, 2016

(54) PCR DIAGNOSTICS OF DERMATOPHYTES AND OTHER PATHOGENIC FUNGI

(71) Applicant: Statens Serum Institut, Copenhagen S (DK)

(72) Inventor: Anna H. Brillowska-Dabrowska, Gdansk (PL)

(73) Assignee: Statens Serum Institut, Copenhagen S. (DK)

( * ) Notice: Subject to any disclaimer, the term of this patent is extended or adjusted under 35 U.S.C. 154(b) by 144 days.

(21) Appl. No.: 14/175,853

(22) Filed: Feb. 7, 2014

(65) Prior Publication Data

US 2014/0154696 A1 Jun. 5, 2014

Related U.S. Application Data

(63) Continuation of application No. 11/917,437, filed as application No. PCT/DK2006/000332 on Jun. 13, 2006, now abandoned.

(30) Foreign Application Priority Data

Jun. 14, 2005 (DK) ................................ 2005 00865
Sep. 10, 2005 (DK) ................................ 2005 01267

(51) Int. Cl.
*C12N 15/10* (2006.01)
*C12Q 1/68* (2006.01)

(52) U.S. Cl.
CPC ......... *C12Q 1/6895* (2013.01); *C12N 15/1003* (2013.01); *C12Q 2600/16* (2013.01)

(58) Field of Classification Search
None
See application file for complete search history.

(56) References Cited

U.S. PATENT DOCUMENTS

2002/0098487 A1 7/2002 Yokoyama et al.
2007/0043216 A1 2/2007 Bair et al.

FOREIGN PATENT DOCUMENTS

WO WO 00/73499 A2 12/2000

OTHER PUBLICATIONS

Ronaghi et al. (2001) genome Res. vol. 11: 3-11.*
Al-Soud, Effects of Amplification Facilitators on Diagnostic PCT in the Presence of Blood, Feces, and Meat, J. Clin. Microbiol., vol. 38, No. 12, pp. 4463-4470, Dec. 2000.
Bock, Diagnostik von Dermatomykosen mit der Polymerase-Kettenreaktion [Detection of dermatophytes by polymerase chain reaction], English-language "Summary" (abstract) included, vol. 48, pp. 175-178, 1997.
Dodgson, Multilocus Sequence Typing of Candida glabrata Reveals Geographically Enriched Clades, Dec. 2003, J. Clin. Microbiol., vol. 41, No. 12, pp. 5709-5717.
Faggi, PCR Fingerprinting for Identification of Common Species of Dermatophytes, Dec. 2002, J. Clin. Microbiol., Letters to the Editors, vol. 40, No. 12, pp. 4804-4805.
Gaedick, Genetic Heterogeneity in the rRNA Gene Locus of Trichophyton tonsurans, Dec. 2003, J. Clin. Microbiol., vol. 41, No. 12, pp. 5478-5487.
Hainer, Dermatophyte Infections, Jan. 1, 2003, American Family Physician, vol. 67, No. 1, pp. 101-108.
Holmes, Detection of *Candida albicans* and Other Yeasts in Blood by PCR, J. Clin. Microbiol., Jan. 1994, vol. 32, No. 1, pp. 228-231.
Invitrogen, Taq DNA Polymerase PCR Buffer, Cat. No. 18067-017, Rev. Date Jan. 2, 2007 [Further information unknown—on Feb. 1, 2011 in parent U.S. Appl. No. 11/917,437].
Jin, Simple Chemical Extraction Method for DNA Isolation from *Aspergillus fumigatus* and Other *Aspergillus*Species, J. Clin. Microbiol., Sep. 2004, pp. 4293-4296.
Kanbe, PCR-Based Identification of Common Dermatophyte Species Using Primer Sets Specific for the DNA Topoisomerase II Genes, 2003, J. Dermatological Science, vol. 32, pp. 151-161.
Kano, Chitin Synthase 1 (Chs1) Gene Sequences of Microsporum equinum and Trichophyton equinum, 2001, Veterinary Microbiology, vol. 78, pp. 85-90.
Kano, Detection of Microsporum canis in the Skin Scrapings and Hair of Dogs with Dermatophytosis Based on Sequences of the Chitin Synthase 1 Gene, 2000, Microbiology and Immunology, vol. 44, No. 7, pp. 605-607.
Kano, Differentiation of Microsporum Species by Random Amplification of Polymorphic DNA (RAPD) and Souther Hybridization Analysis, 1998, Mycoses, vol. 41, pp. 229-233.
Kano, Direct Detection of Dermatophytes in Skin Samples Based on Sequences of the Chitin Synthase 1 (CHSI) Gene, Feb. 2003, J. Veterinary Medical Science, vol. 65, No. 2, pp. 267-270.
Kano, Species-Specific Primers of Chitin Synthase 1 Gene for the Differentiation of the Trichophytin mentagrophytes Complex, Jan. 1999, Mycoses, vol. 42, Issues 1-2, pp. 71-74.
Kristiansen, Identification of Mycorrhizal Fungi from Single Pelotons of Dactylorhiza majalis (Orchidaceae) Using Single-Strand Conformation Polymorphism and Mitochondrial Ribosomal Large Subunit DNA Sequences, 2001, Molecular Ecology, vol. 10, pp. 2089-2093.

(Continued)

*Primary Examiner* — Suchira Pande
(74) *Attorney, Agent, or Firm* — Howson & Howson, LLP

(57) ABSTRACT

Dermatophytes which belong to one of the three genera *Epidermophyton*, *Trichophyton* and *Microsporum* are the main cause of fungal infections of skin, hair and nails. Traditional diagnostic procedures consist of microscopy and culture, but due to the slow growth rate of dermatophytes typically two to four weeks are needed before a final diagnosis is obtained. The present invention is a rapid DNA extraction method extracting nucleic acids from fungi (e.g. dermatophytes and other pathogenic fungi) which can be performed from directly on hair, nail or skin specimens from humans, from naturally or experimentally infected animals or from cultured fungal colonies for the use in PCR amplification and detection assays. The present invention also includes specific primer sets for detection of any dermatophyte and for species specific detection of *Trichophyton rubrum* and *Epidermophyton floccosum* by PCR and a kit for diagnosing fungal infections.

10 Claims, 11 Drawing Sheets

(56) References Cited

OTHER PUBLICATIONS

Liu, Application of PCR to the Identification of Dermatophyte Fungi, 2000, Journal of Medical Microbiology, vol. 49, pp. 493-497.
Liu, Molecular Determination of Dermatophyte Fungi Using the Arbitrarily Primed Polymerase Chain Reaction, 1997, British Journal of Dermatology, vol. 137, No. 351-355.
Liu, Rapid Mini-Preparation of Fungal DNA for PCR, Jan. 2000, J. Clin. Microbiol., vol. 38, No. 1, p. 471.
Machouart-Dubach, Rapid Discrimination Among Dermatophytes, *Scytalidium* spp., and Other Fungi with a PCR-Restriction Fragment Length Polymorphism Ribotyping Method, Feb. 2001, J. Clin. Microbiol., vol. 39, No. 2, pp. 685-690.
Muller, Rapid Extraction of Genomic DNA from Medically Important Yeasts and Filamentous Fungi by High-Speed Cell Disruption, Jun. 1998, J. Clin. Microbiol., vol. 36, No. 6, pp. 1625-1629.
NHO, Species Differentiation by Internally Transcribed Spacer PCR and *Hhal* Digestion of Fluconazole-Resistant *Candida krusei, Candida inconspicua,* and *Candida norvegensis* Strains, J. Clin. Microbiol., Apr. 1997, vol. 35, No. 4, pp. 1036-1039.
NINET, Identification of Dermatophyte Species by 28S Ribosomal DNA Sequencing With a Commercial Kit, Feb. 2003, J. Clin. Microbiol., vol. 41, No. 2, pp. 826-830.
QIAGEN, QIAamp DNA FFPE Tissue Handbook, Oct. 2007.
QIAGEN, QIAamp DNA Mini and Blood Mini Handbook, Nov. 2007.
Shin, Species Identification and Strain Differentiation of Dermatophyte Fungi Using Polymerase Chain Reaction Amplification and Restriction Enzyme Analysis, Jun. 2003, J. American Academy of Dermatology, vol. 48, No. 6, pp. 857-865.
Sigma-Aldrich, 2002-2003 Catalog, p. 824 [Further information unknown—on Feb. 1, 2011 in parent U.S. Appl. No. 11/917,437].
Sigma-Aldrich, XNAT2 Extract-N-Amp Tissue PCR Kit, printed Jan. 26, 2011 [Further information unknown—on Feb. 1, 2011 in parent U.S. Appl. No. 11/917,437].
Sreenivasaprasad, Isolation of Fungal Nucleic Acids, Nucleic Acid Protocols Handbook, pp. 67-45, R. Rapley (editor), Humana Press, Inc., Totowa, NJ, 2000.
Statens Serum Institut, Dermatophyte PCR Kit (information), 2nd Edition, Apr. 2013.
Tavanti, Optimization and Validation of Multilocus Sequence Typing for Candida albicans, Aug. 2003, J. Clin. Microbiol., vol. 41, No. 8, pp. 3765-3776.
Wang, A High-Throughput System for the Rapid Extraction of Plant Genomic DNA for Genome Mapping and Marker-Assisted Breeding Studies, Aug. 2005, J. Association for Laboratory Automation, pp. 242-245.
Weig, Usefulness of PCR for Diagnosis of *Pneumocystis carinii* Pneumonia in Different Patient Groups, Jun. 1997, vol. 35, No. 6, pp. 1445-1449.
Wikipedia, Chelex 100, Entry printed on Jan. 25, 2011 [Further information unknown—on Feb. 1, 2011 in parent U.S. Appl. No. 11/917,437].
Jul. 13, 2011 Communication in European Patent Application No. EP06753306.7 (regional stage of PCT/KD2006/000332, from which the present application claims priority)—See PTC/SB/20EP PPH Request.
Suenaga, et al., Evaluation of three methods for effective extraction of DNA from human hair, J. Chrom. B., 820 (2005):137-141; published online Apr. 11, 2005.
High Pure PCR Template Preparation Kit, Version 16.0, Dec. 2008, Roche Applied Science.
Liu, et al., Application of PCR to the identification of dermatophyte fungi, J. Med. Microbiol., vol. 49 (2000), 493-497, Jun. 2000.

\* cited by examiner

Gr: the result of culture
M: the result of microscopy
Tr: result of *Trichophyton rubrum* specific PCR
Der: result of pandermatophyte PCR
(-): negative
(+): positive

SEQUENCE LISTING

```
<160> NUMBER OF SEQ ID NOS: 17

<210> SEQ ID NO 1
<211> LENGTH: 27
<212> TYPE: DNA
<213> ORGANISM: Dermatophyt sp.

<400> SEQUENCE: 1
gaagaagatt gtcgtttgca tcgtctc                                        27

<210> SEQ ID NO 2
<211> LENGTH: 24
<212> TYPE: DNA
<213> ORGANISM: Dermatophyt sp.

<400> SEQUENCE: 2
ctcgaggtca aaagcacgcc agag                                           24

<210> SEQ ID NO 3
<211> LENGTH: 21
<212> TYPE: DNA
<213> ORGANISM: Dermatophyt sp.

<400> SEQUENCE: 3
tctttgaacg cacattgcgc c                                              21

<210> SEQ ID NO 4
<211> LENGTH: 21
<212> TYPE: DNA
<213> ORGANISM: Trichophyton rubrum

<400> SEQUENCE: 4
tctttgaacg cacattgcgc c                                              21
```

-continued

```
<210> SEQ ID NO 5
<211> LENGTH: 22
<212> TYPE: DNA
<213> ORGANISM: Epidermophyton floccosum

<400> SEQUENCE: 5
ccgacggaaa ctagggccag ag                                          22

<210> SEQ ID NO 6
<211> LENGTH: 26
<212> TYPE: DNA
<213> ORGANISM: Microsporum canis

<400> SEQUENCE: 6
acgtctccat ccaggctgtg ctctcc                                      26

<210> SEQ ID NO 7
<211> LENGTH: 27
<212> TYPE: DNA
<213> ORGANISM: Microsporum canis

<400> SEQUENCE: 7
gcgaggtgtt agaaggaaaa acggtcc                                     27

<210> SEQ ID NO 8
<211> LENGTH: 23
<212> TYPE: DNA
<213> ORGANISM: Trichophyton mentagrophytes

<400> SEQUENCE: 8
gcaagacatg gggtaaagaa gcc                                         23

<210> SEQ ID NO 9
<211> LENGTH: 24
<212> TYPE: DNA
<213> ORGANISM: Trichophyton mentagrophytes

<400> SEQUENCE: 9
gcctatctgg gtggtatatt cgtg                                        24

<210> SEQ ID NO 10
<211> LENGTH: 21
<212> TYPE: DNA
<213> ORGANISM: Microsporum genus

<400> SEQUENCE: 10
ggctcctggg cgaatgggac a                                           21

<210> SEQ ID NO 11
<211> LENGTH: 26
<212> TYPE: DNA
<213> ORGANISM: Microsporum genus

<400> SEQUENCE: 11
ttcagcgggt atccctacct gatccg                                      26

<210> SEQ ID NO 12
<211> LENGTH: 19
<212> TYPE: DNA
<213> ORGANISM: Trichophyton genus

<400> SEQUENCE: 12
ggtgaactgc ggaaggatc                                              19
```

-continued

```
<210> SEQ ID NO 13
<211> LENGTH: 21
<212> TYPE: DNA
<213> ORGANISM: Trichophyton genus

<400> SEQUENCE: 13
acgctcagac tgacagctct t                                          21

<210> SEQ ID NO 14
<211> LENGTH: 26
<212> TYPE: DNA
<213> ORGANISM: Saccharomyces cerevisiae

<400> SEQUENCE: 14
aggtctattc gtattggtat ccaagc                                     26

<210> SEQ ID NO 15
<211> LENGTH: 23
<212> TYPE: DNA
<213> ORGANISM: Saccharomyces cerevisiae

<400> SEQUENCE: 15
ccagtaagtt ccttcatcag aca                                        23

<210> SEQ ID NO 16
<211> LENGTH: 25
<212> TYPE: DNA
<213> ORGANISM: Pichia pastoris

<400> SEQUENCE: 16
cggatcaatt atggtgacga gtagg                                      25

<210> SEQ ID NO 17
<211> LENGTH: 27
<212> TYPE: DNA
<213> ORGANISM: Pichia pastoris

<400> SEQUENCE: 17
aggaacagtt tgtgggttca aatcagg                                    27
```

PCR DIAGNOSTICS OF DERMATOPHYTES AND OTHER PATHOGENIC FUNGI

CROSS-REFERENCE TO RELATED APPLICATIONS

This application is a continuation of U.S. patent application Ser. No. 11/917,437, filed Dec. 13, 2007, which is a national stage of International Patent Application No. PCT/DK06/000332, filed Jun. 13, 2006, which applications are incorporated by reference herein in their entireties.

FIELD OF INVENTION

A method for extracting nucleic acids from fungi, a PCR method for detecting fungi in patient samples and a PCR kit for detecting dermatophytes and diagnosing infections by the three genera *Trichophyton*, *Microsporum* and *Epidermophyton*.

GENERAL BACKGROUND

Human pathogenic dermatophytes, which belong to the three genera *Trichophyton*, *Microsporum* and *Epidermophyton*, are fungi that infect human skin, nails, and hair. While the genus *Epidermophyton* is represented only by a single species (*E. floccosum*), the genera *Microsporum* and *Trichophyton* include several different species (1). Depending on the site of the infection the dermatophytosis can be divided in: Tinea barbae, an infection of the bearded area mainly caused by *T. verrucosum* and *T. mentagrophytes*; Tinea capitis, usually caused by organisms from genera *Microsporum* and *Trichophyton*; Tinea corporis by any of the human pathogenic dermatophytes; Tinea favosa by *T. schoenleninii*; Tinea pedis frequently caused by *T. mentagrophytes*, *E. floccosum* and *T. rubrum*; Tinea mannum caused by *T. rubrum* and Tinea unguinum (also termed onychomycosis) mainly caused by *T. rubrum* and *T. mentagrophytes* (1). Prevalence rates of onychymycosis in European countries vary between 3 and 22% (2). Thus, in a study by Summerbell et al. including 2662 nails, the following infective agents were isolated: *T. rubrum* (>70%), *T. mentagrophytes* (20%), *Candida albicans* (5.5%), and *Scopulariopsis brevicaulis* or non-dermatophyte moulds (1.6%) (3). Tinea unguium is the form of dermatophytosis that is most refractory to treatment and also relapses of infection in clinically cured nails are common (4). Evans et al. (5) compared the efficacy of terbinafine and itraconazole treatment of onychomycosis and showed that mycological cure was achieved in 76% of patients receiving terbinafine but only in 38% receiving itraconazole. In a later study also by Evans et al. the percentage of patients with mycological failure after standard treatment was 20% (6).

Topical therapy is sufficient in most of cases of dermatophyte skin infection, but long term and often expensive systemic treatment is necessary in cases of tinea capitis, tinea barbae and onychomycosis. Various side effects are associated with the systemic antifungals, e.g. gastro-intestinal side effects occur in 3-5% of the patients treated orally with terbinafine and—although less frequent—bone marrow suppression and hepatic side effects occur, why the liver function should be evaluated at baseline and periodically during treatment (7). The diagnosis of onychomycosis should be confirmed before therapy is initiated partly because of the complications associated with the treatment but also because other medical conditions and trauma may cause nail changes that may resemble onychomycosis (8).

Furthermore, genus and in some cases even the species-specific diagnosis is necessary due to different susceptibility patterns and contagious potential of the various dermatophytes, thus e.g. *Microsporum* species are less susceptible than *Trichophyton* spp. to terbinafine and should be treated with griseofulvin, *T. rubrum* strains are more susceptible to some antifungal drugs than *T. mentagrophytes* and some dermatophytes may cause epidemic outbreaks in schools and institutions due to transfer from man to man while others may not as their primary host is an animal (10).

The current diagnosis of dermatophytes is based on microscopic identification of spores and hyphae in clinical specimens followed by in vitro culture and morphological identification of the fungus (1). Direct microscopic examination of skin and nail material is often sufficient for the preemptive diagnosis of a fungal infection, but it does not give specific species diagnosis. Furthermore, although rapid and cheap, this technique has a relatively low sensitivity and shows false negative results in up to 15% cases (2). Application of culture enables specific species identification in 10-15 days in approximately 95% of cases. However, for some slow growing or atypical isolates time to diagnosis is up to 3-4 weeks. Such cases are especially cost- and time-consuming and require specialist skills (2).

It is thus obvious that a simple, rapid and specific method for the diagnosis of dermatophyte infections is necessary. Introduction of a PCR based methodology would increase specificity, simplicity, speed and on the same time be inexpensive.

For studies on species identification and typing, PCR (3,4) PCR fingerprinting (5), random amplification of polymorphic DNA (RAPD) (6), PCR and restriction fragment length polymorphism (RFLP) (7), arbitrarily primed PCR (AP-PCR) (8) have been applied. The main targets have been the following genes or DNA fragments: rDNA region, DNA topoisomerases II genes (11,14). chitin synthase gene (18).

A simple and fast extraction method of the DNA directly from patient samples is necessary for routine application of a molecular based detection methodology of dermatophyte infections. In previously published studies on the use of PCR for identification and/or typing of dermatophyte cultures, typically two steps are involved—disruption of fungi cells and subsequent DNA purification. The disruption of the fungal cells has been performed by mechanical disruption of the cell (grinding, freezing-thawing repeated steps, bead-beating) (16) and/or by chemical lysis (9) of the cell wall: enzymatic (proteinase K, zymolase) (12) or detergent lysis (10,15). The purification of the DNA from disrupted cells has been performed by application of phenol-chlorophorm (12,15) extraction method, by precipitation of DNA (10), or by using DNA's affinity to some specific resins (11) (commercial kits for purification of the DNA).

Such methodologies are inconvenient for routine diagnostic purposes for several reasons. First, the necessary initial cultivation of the patient samples is time consuming (up to 10 days) (13). Next, the phenol/chlorophorm DNA extraction method applied in the methods of the DNA extraction directly from skin and hair samples (14) is toxic and thus not applicable for routine diagnostic use in laboratories receiving a large number of samples per day. Finally, the previously published methods all involve a number of handlings (e.g. grinding or bead beating, and washing of the DNA pellets or columns) that increase the risk of the contamination of the samples and false PCR results. In agreement with this, PCR based diagnostic methods are not applied at a routine basis at any diagnostic laboratory to our knowledge, neither in Denmark nor worldwide.

The present invention solves this problem by disclosing a PCR based diagnosis of dermatophyte infections after a simple DNA extraction method which can be applied directly on clinical specimens.

SUMMARY OF THE INVENTION

We have developed a) a DNA extraction method from yeasts (e.g. *Candida albicans, Candida glabrata, Pichia pastoris, Sacharomyces cerevisiae*) and molds, especially keratinophylic fungi and b) a PCR based method that allows the detection of dermatophyte infections directly on patient samples (such as nails, hair, and skin). In a three steps procedure the method enables the extraction of DNA from e.g. nail samples and enables the diagnosis of infections caused by any of the dermatophytes (pan-dermatophyte). It enables also the detection of genera-specific detection of species belonging to *Microsporum* and *Trichophyton* genera. Species specific detection can be performed by application of the procedure that enables to examine *Trichophyton rubrum, Microsprorum canis, Trichophyton mentagrophytes-Trichophyton tonsurans* complex and *Epidermophyton floccosum* infection. The methods of the invention are provided as diagnostic methods for detecting dermatophytosis-associated DNA of fungi in human.

DETAILED DISCLOSURE OF THE INVENTION

Definitions

Dermatophytes: a group of keratinophilic fungi formed by species belonging to three genera: *Trichophyton, Epidermophyton* and *Microsporum* pan-dermatophytes PCR: PCR reaction where one primer set targeting a common sequence shared by the group of dermatophytes, amplifies a common gene sequence and thus makes it possible to detect all species belonging to *Trichophyton, Epidermophyton* and *Microsporum* genera.

multiplex PCR: a reaction that amplifies multiple DNA fragments (in one PCR reaction). The use of several primer sets for detection of several species at the same time. In this case the pan-dermatophyte primer set for the detection of all dermatophytes and one or more species specific primer sets for the identification in the same step of one or more of the species. In the case of nail infection for instance the vast majority of the infections are caused by *T. rubrum* so a set up with a pan-dermatophyte primer set and a *T. rubrum* specific primerset will answer two questions at one time—is there a dermatophyte infection at all and if so is it then the most common one or not.

The present invention discloses a method of extracting nucleic acid from fungi comprising the steps of heating the sample in a lysis buffer and subsequent mixing the solution with a neutralizing buffer, where the lysis buffer consists of a reducer, a salt and a buffering compound in an aqueous solution and the neutralizing buffer is a 0.5-3% w/v, preferably a 2% w/v protein solution. The target fungi belong to the group of yeasts (e.g. *Candida albicans, Candida glabrata, Pichia pastoris, Sacharomyces cerevisiae*) and molds, especially keratinophylic fungi, dermatophytes, which are species belonging to the genera *Trichophyton, Epidermophyton* or *Microsporum*. The reducer in the lysis buffer is chosen from sodium carbonate, sodium sulfite, beta-mercaptoethanol, dithioreitol, sodium sulfide, sodium chlorate, sodium iodate and sodium bicarbonate, the salt is chosen from potassium chloride and ammonium persulfate and where the buffering compound is chosen from sodium salt of 3-(Cyclohexylamino)-2-hydroxy-1-propanesulfonic acid, TRIS, HEPES, phosphate buffer. A preferred lysis buffer consists of potassium chloride (KCl), sodium bicarbonate (NaHCO$_3$) and tris(hydroxymethyl)aminomethane (TRIS). The sample in lysis buffer is heated to between 80 and 100° C., preferably 95° C. for app. 10 minutes. The protein in the neutralizing buffer can be chosen from bovine serum albumin (BSA), ovalbumin or other suitable protein.

The present invention also discloses a method for the detection of fungi in patient samples comprising extracting nucleic acid from the sample according to above mentioned extraction method, amplifying the nucleic acid with PCR using fungus specific primers and detecting fungus specific gene-sequences. Detection of the fungal PCR-amplicons can be performed by any method known in the art e.g. electrophoresis, probe hybridisation etc.

A preferred detection is the detection of dermatophytes in general or specific keratinophylic fungal species belonging to the genera *Trichophyton, Epidermophyton* or *Microsporum*. General detection of dermatophytes using PCR is described and specific detection of *T. rubrum, Microsporum canis, Trichophyton mentagrophytes-Trichophyton tonsurans* complex or *E. floccosum* is also described. A method of detecting infections with fungi using multiplex PCR is described and the preferred embodiment of the invention. Specific primers for above mentioned detection and diagnosis are disclosed.

The invention also discloses new primers for PCR amplification of dermatophytes sequences comprising the nucleotide sequences SEQ ID NO. 1, 2, 3, 4, 5, 6, 7, 8 and 9.

The invention also discloses a kit for performing the diagnosis of dermatophytes infection using PCR, where the kit comprises above mentioned lysis buffer, neutralising buffer, primers for performing the PCR and optionally the other ingredients for performing a PCR amplification and detection (e.g. polymerase, buffers, probes etc).

The present invention is directed to a high-throughput assay useful for rapid screening a large number of samples to detect a DNA sequence of dermatophytes. The method of the present invention is especially useful for extracting fungi DNA from colonized or infected hair, nail or skin from humans or animals for use in a high throughput screening assay including, but not limited to, a polymerase chain reaction (PCR), ligase chain reaction (LCR), or other conventional DNA detection assay for the detection of DNA.

The invention provides the sequence tags for application in the detection of DNA of specific genetic sequences at low copy numbers.

The methods of the invention comprise means of extracting DNA from nail, hair or skin in a first step, selective amplification and detection of dermatophyte DNA-sequences in a second step and/or selective amplifying and detecting of species-specific dermatophyte DNA-sequences e.g. the *Microsporum canis, Trichophyton mentagrophytes-Trichophyton tonsurans* complex, *Trichophyton rubrum* or *Epidermophyton floccosum* DNA.

Extraction of fungal DNA from human samples (skin, hair or nail) is performed in the two step procedure:
1. Heating of the sample in an aqueous lysis buffer and
2. Mixing the solution with an aqueous neutralizing buffer
The aqueous lysis buffer consists of:
  a reducer (e.g. sodium carbonate, sodium sulfite, beta-mercaptoethanol, dithiotreitol-DTT, sodium sulfide, sodium chlorate, sodium chlorite, sodium iodate, sodium bicarbonate),
  salt (potassium chloride, ammonium persulfate), a buffering compound (sodium salt of 3-(Cyclohexylamino)-2-hydroxy-1-propanesulfonic acid—CAPSO, tris(hydroxymethyl)aminomethane—TRIS, 4-(2-Hydroxyethyl)piperazine-1-ethanesulfonic acid—HEPES, phosphate buffer)

The constitution of lysis buffer consists of a combination of compounds listed above (reducer, salt and buffering compound) can be:

beta-mercaptoethanol, potassium chloride and tris(hydroxymethyl)aminomethane—TRIS, beta-mercaptoethanol, potassium chloride and 4-(2-Hydroxyethyl)piperazine-1-ethanesulfonic acid—HEPES, beta-mercaptoethanol, potassium chloride and phosphate buffer, sodium sulfide, potassium chloride and 4-(2-Hydroxyethyl)piperazine-1-ethanesulfonic acid—HEPES, sodium chlorite, potassium chloride and sodium salt of 3-(Cyclohexylamino)-2-hydroxy-1-propanesulfonic acid—CAPSO, sodium iodate, potassium chloride and Cyclohexylamino)-2-hydroxy-1-propanesulfonic acid—CAPSO, beta-mercaptoethanol, ammonium persulfate and phosphate buffer.

etc.

The preferred constitution of the lysis buffer is:
sodium bicarbonate,
potassium chloride,
tris(hydroxymethyl)aminomethane, pH 9.0, The neutralizing buffer is an aqueous protein solution e.g. bovine serum albumin (BSA), ovalbumin or another suitable protein.

The extraction of DNA from fungi can also be performed with the buffers in Red Extract-N-Amp Plant Kit (SIGMA) and Extract-N-Amp Plant Kit (SIGMA); the buffers in these two kits are the same the only difference being the addition of a red dye in the first mentioned kit (useful on application on gels).

The protein concentration should be in the range 0.5-3% w/v

The preferred constitution of the neutralizing buffer is 2% w/v bovine serum albumin.

Different concentrations of individual components of both solutions were tested, the concentration of sodium bicarbonate (NaHCO$_3$) should be in the range of 8.0-80.0 mM, the content of bovine serum albumin (BSA) should be in the range 0.5-3% in aqueous solution. The preferred formulation of the lysis buffer consist of 250 mM potassium chloride (KCl), 60 mM sodium bicarbonate (NaHCO$_3$), 50 mM tris(hydroxymethyl)aminomethane (Tris).

The admissible pH of the lysis solution is in the range between 7.0 and 12, the preferred pH is 9.5. The solution is prepared by adding NaHCO$_3$, KCl, Tris to DNases, RNases free water and sterilization grade filtrated by 0.22 μm pore size filter. The resulting solution is stored frozen at minus 22° C.

The preferred concentration of bovine serum albumin (BSA) in neutralizing buffer is 2%. The solution is prepared by adding adequate amount of bovine serum albumin (BSA) to water and filter sterilizing through a 0.22 μm filter. The resulting solution is stored frozen at minus 22° C.

The preferred temperature of heating of the sample in lysis buffer is 95° C., however 80° C. is sufficient. The preferred time of heating of the sample in lysis buffer is 10 minutes. It should not exceed 10 minutes, due to increasing possibility of the DNA degradation.

DNA extracted from hair, skin or nail by mean of the method described above (or which can be by any of the methods described previously [9, 10, 12, 15, 16]) is amplified by polymerase chain reaction (PCR) (or can be amplified by any of previously described method [3, 4, 5, 6, 7, 8]).

Primers used in the amplification are based on the dermatophyte specific, *Trichophyton rubrum*, *Trichophyton mentagrophytes-Trichophyton tonsurans* complex, *Microsporum canis* or *Epidermophyton floccosum* specific DNA sequences (Example 1) and are listed below.

The invention provides the following primers, oligonucleotides, enable to determine the dermatophyte species

```
panDerm1
                                      [SEQ ID NO. 1]
(5'GAAGAAGATTGTCGTTTGCATCGTCTC 3')

panDerm2
                                      [SEQ ID NO. 2]
(5'CTCGAGGTCAAAAGCACGCCAGAG 3')

uni
                                      [SEQ ID NO. 3]
(5' TCTTTGAACGCACATTGCGCC 3')

Trubrum-rev
                                      [SEQ ID NO. 4]
(5'CGGTCCTGAGGGCGCTGAA3')

Ef-rev
                                      [SEQ ID NO. 5]
(5'CCGACGGAAACTAGGGCCAGAG 3')

Mc-for
                                      [SEQ ID NO. 6]
(5' ACGTCTCCATCCAGGCTGTGCTCTCC 3')

Mc-rev
                                      [SEQ ID NO. 7]
(5'GCGAGGTGTTAGAAGGAAAAACGGTCC 3')

TmTt-for
                                      [SEQ ID NO. 8]
(5' GCAAGACATGGGGTAAAGAAGCC 3')

TmTt-rev
                                      [SEQ ID NO. 9]
(5' GCCTATCTGGGTGGTATATTCGTG 3')

Micr773-for
                                      [SEQ ID NO. 10]
(5'GGCTCCTGGGCGAATGGGACA 3')

Micr885-rev
                                      [SEQ ID NO. 11]
(5' TTCAGCGGGTATCCCTACCTGATCCG 3')

Trichopyros-for
                                      [SEQ ID NO. 12]
(5' GGTGAACTGCGGAAGGATC 3')

Trichopyros-rev
                                      [SEQ ID NO. 13]
(5' ACGCTCAGACTGACAGCTCTT 3')
``` and their derivatives.

The sequences of panDerm1 and panDerm2 derive from the chitin synthase 1 (chs1) gene, which is common for all of the dermatophytes.

The sequences of uni, derives from ITS2 (internal transcribed spacer) of dermatophytes.

The sequences of Trubrum-rev and Ef-rev derive from ITS2 (internal transcribed spacer) of *Trichophyton rubrum* or *Epidermophyton floccosum* respectively.

The sequences of Mc-for and Mc-rev derived from actin gene of *Microsporum canis*.

The sequences of TmTt-for and TmTt-rev derived from chitin synthase gene of *Trichophyton mentagrophytes* and *Trichophyton tonsurans*.

The sequences of Micr773-for, Micr885-rev, Trichopyros-for and Trichopyros-rev derive from rDNA (ribosomal DNA) of *Microsporum* genus or *Trichophyton* genus respectively Derivatives of panDerm1, panDerm2, uni, Trubrum-rev, Ef-rev, TmTt-for, TmTt-rev, Mc-for, Mc-rev include fragments of panDerm1, panDerm2, uni, Trubrum-rev, Ef-rev, TmTt-for, TmTt-rev Mc-for, Mc-rev, Micr773-for, Micr885-rev, Trichopyros-for and Trichopyros-rev of at least 10 nucleotides in length and oligonucleotides which comprise such fragments.

Oligonucleotides panDerm1 and panDerm2 are used as a pair of primers for the detection of the dermatophyte DNA in a sample. Oligonucleotides uni and Trubrum-rev are used as a pair of primers for the detection of the *Trichophyton rubrum* DNA in a sample. Oligonucleotides uni and Ef-rev are used as a pair of primers for the detection of the *Epidermophyton floccosum* DNA in a sample. Oligonucleotides Mc-for and Mc-rev are used as a pair of primers for the detection of the *Microsporum canis* DNA in a sample. Oligonucleotides TmTt-for and TmTt-rev are used as a pair of primers for the detection of the *Trichophyton mentagrophytes-Trichophyton tonsurans* complex DNA in a sample. Oligonucleotides Micr773-for and Micr885-rev are used as a pair of primers for the detection of the *Microsporum* DNA in a sample. Oligonucleotides Trichopyros-for and Trichopyros-rev are used as a pair of primers for the detection of the *Trichophyton* DNA in a sample.

Oligonucleotides panDerm1 together with panDerm2 and uni together with Trubrum-rev are used as two pair of primers for the simultaneous detection of *Trichophyton rubrum* DNA and/or any dermatophyte DNA in a sample.

Oligonucleotides panDerm1 together with panDerm2 and uni together with Ef-rev are used as two pair of primers for the detection of the *Epidermophyton floccosum* DNA and/or any dermatophyte DNA in a sample.

Oligonucleotides panDerm1 together with panDerm2 and TmTt-for together with TmTt-rev are used as two pair of primers for the detection of the *Trichophyton mentagrophytes-Trichophyton tonsurans* complex DNA and/or any dermatophyte DNA in a sample.

Oligonucleotides panDerm1 together with panDerm2 and Mc-for together with Mc-rev are used as two pair of primers for the simultaneous detection of *Microsporum canis* DNA and/or any dermatophyte DNA in a sample.

Oligonucleotides Micr773-for together with Micr885-rev and Trichopyros-for together with Trichopyros-rev are used as a two pair of primers for the simultaneous detection of *Microsporum* genus and/or *Trichophyton* genus DNA.

Oligonucleotides Trichopyros-for together with Trichopyros-rev and uni together with Trubrum-rev are used as two pair of primers for the simultaneous detection of *Trichophyton* genus DNA and/or *Trichophyton rubrum* DNA.

Oligonucleotides Trichopyros-for together with Trichopyros-rev and TmTt-for together with TmTt-rev are used as two pair of primers for the detection of *Trichophyton genus* DNA and/or the *Trichophyton mentagrophytes-Trichophyton tonsurans* complex DNA in a sample.

Oligonucleotides Trichopyros-for together with Trichopyros-rev, uni together with Trubrum-rev and TmTt-for together with TmTt-rev are used as three pair of primers for the detection of *Trichophyton genus* DNA and/or *Trichophyton rubrum* DNA and/or the *Trichophyton mentagrophytes-Trichophyton tonsurans* complex DNA in a sample.

Oligonucleotides panDerm1, panDerm2, uni, Trubrum-rev and Ef-rev are used in combination as primers for the detection of *Trichophyton rubrum* DNA and/or *Epidermophyton floccosum* DNA and/or any dermatophyte DNA in a sample.

Oligonucleotides Micr773-for together with Micr885-rev and uni together with Ef-rev are used as a primers for the simultaneous detection of *Microsporum* genus and/or *Epidermophyton floccosum* DNA.

Oligonucleotides panDerm1, panDerm2, uni, Trubrum-rev, Ef-rev, Mc-for and Mc-rev are used in combination as primers for the detection of *Trichophyton rubrum* DNA and/or *Epidermophyton floccosum* DNA and/or *Microsporum canis* DNA and/or any dermatophyte DNA in a sample.

Oligonucleotides uni, Trubrum-rev, Ef-rev, Mc-for, Mc-rev, TmTt-for and TmTt-rev are used in combination as four pair of primers (uni together with Trubrum-rev and uni together with Ef-rev, Mc-for together with Mc-rev, and TmTt-for together with TmTt-rev) for the detection of the *Epidermophyton floccosum* DNA and/or *Microsporum canis* DNA, and/or *Trichophyton mentagrophytes-Trichophyton tonsurans* complex and/or *Trichophyton rubrum* DNA.

Any known techniques for nucleic acid (e.g., DNA and RNA) amplification can be used with the assays described herein. Preferred amplification technique is the polymerase chain reaction (PCR) methodologies which comprise solution PCR to detect the presence or absence of unique sequences of any dermatophyte, *Trichophyton* genus, *Microsporum* genus, *Trichophyton rubrum*, *Microsporum canis*, *Trichophyton mentagrophytes-Trichophyton tonsurans* complex and/or *Epidermophyton floccosum*.

The PCR reaction using the oligonucleotides is performed as follows: denaturation at 93-98° C. for 3-10 minutes, preferably 95° C. for 5 minutes, then 30-45 cycles, preferably 45 cycles of amplification, one cycle represents:

denaturation at 93-98° C. for 0.5-3 minutes, preferably 94° C. for 40 sec, primer annealing at 55-65° C. for 0.5-3 minutes, preferably 60° C. for 1 min, elongation at 72° C. for 0.5-3 minutes, preferably for 1 min.

After 45th cycle the samples are incubated 3-15 minutes, preferably 10 minutes at 72° C.

There are numerous methods to detect amplified DNA e.g. capilar electrophoresis, DNA-DNA hybridization, any of which may be used.

If the specific band:
366 bp (for dermatophyte) of chitin synthase gene fragment is detected, a dermatophyte infection can be assumed.

If the specific band:
115 bp (for genus *Microsporum*) of rDNA (ribosomal DNA) fragment
258 bp (for genus *Trichophyton*) of rDNA (ribosomal DNA) fragment Is detected, a *Microsporum* genus or *Trichophyton* genus infection can be assumed.

If the specific band
202 bp (for *Trichophyton rubrum*) of ITS2 (internal transcribed spacer) fragment of rDNA or
259 bp (for *Epidermophyton floccosum*) of ITS2 fragment or
520 bp (for *Microsporum canis*) of actin gene or
129 bp (for *Trichophyton mentagrophytes-Trichophyton tonsurans* complex) of chitin syntase gene is detected, a specific *Trichophyton rubrum, Epidermophyton floccosum, Microsporum canis* or *Trichophyton mentagrophytes-Trichophyton tonsurans* complex infection can be assumed.

The advantage of the procedure described above is that the dermatophyte infection (on the base of presence of dermatophyte DNA) can be generally detected directly from patient samples (nail, skin or hair), the infection caused by dermatophyte belonging to *Microsporum* genus and/or *Trichopyton* genus, and also *Trichophyton rubrum*, *Epidermophyton floccosum*, *Microsporum canis* or *Trichophyton mentagrophytes-Trichophyton tonsurans* complex infections can be detected.

The described DNA extraction method however, is employed in the process of identification of dermatophyte infection directly from human hair, nail or skin can be used differently. Using the described method the DNA can be extracted from fungi cultured on the plates, slants or any kind of broth. Dermatophyte DNA can also be extracted from hair, skin or nail of naturally or experimentally infected animals.

The DNA extracted by mean of the described method can be applied to any of DNA amplification reaction (polymerase chain reaction—PCR, isothermal nucleic acid sequence based amplification—NASBA, ligase chain reaction—LCR, pyrosequencing) and other sequence replication assays or any combination of them.

The primers described can also be applied in any nucleotide (DNA, RNA) amplification reaction.

The PCR products obtained by application of described primers can be used in pyrosequencing reactions allow for species-specific and/or genus specific detection of any dermatophytes.

Upper row: M—molecular weight marker (100 bp DNA ladder, fragment sizes (bp): 2000, 1900, 1800, . . . , 100), 1-6—results for *Candida albicans*, 7-8—results for *Candida krusei*, 9—result for *Candida albicans*, 10—result for *Candida crusei*, 11—result for *Candida albicans*, 12-13—results for *Candida crusei*, 14-15—results for *Candida albicans*, 16-17—results for *Candida krusei*, 18—result for *Candida albicans*, 19—result for *Candida krusei*

Bottom row: lanes: M—molecular weight marker (100 bp DNA ladder, fragment sizes (bp): 2000, 1900, 1800, . . . , 100), 1—result for *Candida glabrata*, 2—result for *Candida albicans*, 3—result for *Candida glabrata*, 4,5—result for *Microsporum canis*, 6—result for *Candida glabrata*, 7—result for *Candida albicans*, 8—result for *Candida glabrata*, 9—result for *Candida albicans*, 10—result for *Candida glabrata*, 11-12—result for *Candida albicans*, 13-14—result for *Candida glabrata*, 15-16—results for *Candida krusei*, 17—result for *Candida albicans*, 18—result for *Candida krusei*, 19—result for *Candida albicans*

Figure 10:
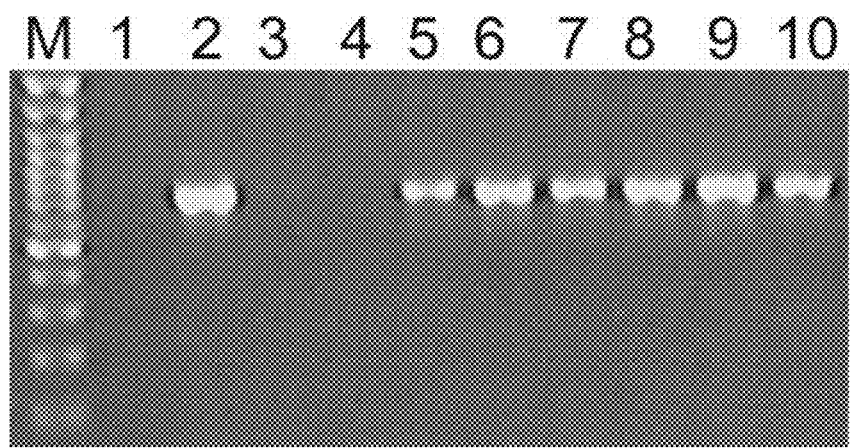

FIG. 10: Example of *Candida glabrata* TRD1 gene amplification (820 bp). Lanes: M—molecular weight marker (100 bp DNA ladder, fragment sizes (bp): 2000, 1900, 1800, . . . , 100), 1—result for *Candida albicans*, 2—result for *Candida glabrata*, 3, 4—result for *Candida albicans*, 5-10—results for *Candida glabrata*

Figure 11:
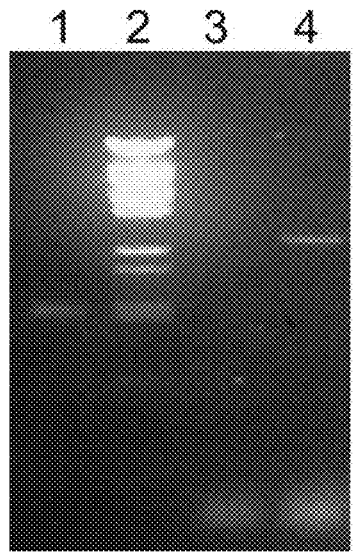

FIG. 11: Example of *Saccharomyces cerevisiae* (1440 bp) and *Pichia pastoris* (2879 bp) genes amplification. Lanes: 1—result for *Sacharomyces cerevisiae*, 2—molecular weight marker (fragment sizes (bp): 7242, 6369, 4822, 4234, 3675, 2323, 2929, 1371, 1264, 702), 3—negative control for *Pichia pastoris* primers, 4—result for *Pichia pastoris*

EXAMPLES

Example 1

Primer Designing

The dermatophyte, *Trichophyton rubrum*, *Microsporum canis*, *Trichophyton mentagrophytes-Trichophyton tonsurans* complex or *Epidermophyton floccosum* specific primers were selected from available DNA sequences listed in Table 1. The alignment of respective sequences allowed the design of primer-pairs detecting all of the dermatophyte species (in case of panDerm1 and panDerm2 oligonucleotides), species belonging to *Microsporum* genus (in case of Micr773-for and Micr885-rev oligonucleotides), species belonging to *Trichophyton* genus (in case of Trichopyros-for and Trichopyros-rev oligonucleotides) and for specific detection of *Trichophyton rubrum*, *Microsporum canis*, *Trichophyton mentagrophytes-Trichophyton tonsurans* complex or *Epidermophyton floccosum*.

TABLE 1

The sequenced used in primers designing.

| | Gene Bank™ accession number (www.ncbi.nih.gov) |
|---|---|
| *Arthoderma benhamiae* | AB044155 |
| *Arthoderma benhamiae* | AB003558 |
| *Arthoderma gypseum* | AB003568 |
| *Arthoderma simii* | AB003564 |
| *Arthoderma vanbreuseghemii* | AB003565 |
| *Arthoderma otae* | AB003563 |
| *Arthoderma incurvatum* | AB003562 |
| *Arthoderma grubyi* | AB003559 |
| *Arthoderma fulvum* | AB003559 |
| *Trichophyton equinum* | AB032479 |
| *Microsporum equinum* | AB015133 |
| *Arthoderma curreyi* | AB050586 |
| *Arthoderma uncinatum* | AB050580 |
| *Trichophyton rubrum* | AJ270807 |
| *Trichophyton rubrum* | AJ270808 |
| *Trichophyton rubrum* | U18352 |
| *Trichophyton rubrum* | Z97993 |
| *Trichophyton raubitschekii* | AJ270802 |
| *Trichophyton raubitschekii* | AJ270803 |
| *Trichophyton raubitschekii* | AJ270804 |
| *Trichophyton raubitschekii* | AJ270805 |
| *Trichophyton rodhaini* | AJ270806 |
| *Arthoderma benhamiae* | AB048193 |
| *Arthoderma benhamiae* | AB105797 |
| *Arthoderma benhamiae* | AB048192 |
| *Trichophyton mentagrophytes* | Z98000 |
| *Trichophyton mentagrophytes* | Z98001 |
| *Trichophyton mentagrophytes* | Z97999 |
| *Trichophyton mentagrophytes* | Z97998 |
| *Trichophyton mentagrophytes* | Z97997 |
| *Trichophyton yaoundei* | AJ270813 |
| *Trichophyton yaoundei* | AJ270812 |
| *Trichophyton equinum* | Z98009 |
| *Trichophyton violaceum* | AJ270810 |
| *Trichophyton violaceum* | AJ270811 |
| *Trichophyton soudanese* | AJ270809 |

TABLE 1-continued

The sequenced used in primers designing.

| | Gene Bank™ accession number (www.ncbi.nih.gov) |
|---|---|
| *Trichophyton schoenleinii* | Z98010 |
| *Trichophyton verrucosum* | Z98002 |
| *Trichophyton tonsurans* | Z98005 |
| *Microsporum canis* | AJ000618 |
| *Microsporum audouinii* | AJ252331 |
| *Microsporum equinum* | AJ252330 |
| *Microsporum distortum* | AJ252329 |
| *Epidermophyton floccosum* | AJ000629 |

Example 2

Evaluation of the Specificity of Dermatophyte, Genus *Trichophyton*, Genus *Microsporum*, *Trichophyton rubrum*, *Epidermophyton floccosum*, *Microsporum canis* and *Trichophyton mentagrophytes-Trichophyton tonsurans* Complex Specific Primers Materials and Methods Strains. A list of the type, references and clinical fungal strains used in the study is presented in Table 2 Twelve strains were obtained from the National Collection of Pathogenic Fungi (United Kingdom). Clinical strains were obtained from Mycology Laboratory of Statens Serum Institute (SSI, Denmark). All clinical isolates were identified by colony characteristics and micro-morphology.

TABLE 2

Microorganism used in the study.

| Microorganism | NCPF number | Number of clinical isolates |
|---|---|---|
| *Microsporum gypseum* | NCPF-40 | 2 |
| *Microsporum canis* | NCPF-177 | 10 |
| *Microsporum nanum* | — | 1 |
| *Microsporum audouinii* | NCPF-436 | 5 |
| *Trichophyton mentagrophytes* var. *mentagrophytes* | NCPF-224 | 10 |
| *Trichophyton mentagrophytes* var. *interdigitale* | NCPF-780 | |
| *Trichophyton schoenleninii* | NCPF-124 | — |
| *Trichophyton terrestre* | NCPF-602 | 8 |
| *Trichophyton rubrum* | NCPF-113 | 12 |
| *Trichophyton tonsurans* | NCPF-690 | 8 |
| *Trichophyton soudanese* | NCPF-800 | 13 |
| *Trichophyton violaceum* | NCPF-794 | — |
| *Trichophyton verrucosum* | — | 6 |
| *Epidermophyton floccosum* | NCPF-777 | 14 |
| *Scopulariopsis brevicalius* | — | 1 |
| *Malassezia furfur* | — | 5 |
| *Candida albicans* | — | 3 |
| *Candida glabrata* | — | 4 |
| *Candida krusei* | — | 2 |
| *Aspergillus niger* | — | 2 |
| *Alternaria* sp. | — | 1 |
| *Acremonium* sp. | — | 1 |
| *Sacharomyces cerevisiae* | — | 2 |

Clinical samples. Ninety-seven nail samples were randomly chosen from clinical samples received at the Laboratory of Mycology at SSI. Twenty-eight were positive by microscopy and culture and were diagnosed as *T. rubrum* (23 cases), *T. mentagrophytes* (3 cases), *Alternaria* sp. (1 case) and *Acremonium* sp. (1 case) and 26 were microscopy-positive but culture negative, why the samples were regarded as dermatophyte positive but no genus nor species identification could be established by traditional methodology.

DNA preparation from dermatophyte cultures. Strains (Table 1) were cultured in 2 ml of Sabouraud liquid medium with and incubated with shaking for up to 8 days at 27° C. After harvest, pellet was resuspended in 500 μl of lysis buffer (400 mM Tris-HCl [pH 8.0], 60 mM EDTA [pH 8.0], 150 mM NaCl, 1% sodium dodecyl sulphate) and left at room temperature for 10 minutes. 150 μl of potassium acetate [pH 4.8] was added and tubes were vortex-mixed and spun down (1 min, 12000×g). The supernatant was transferred to new tube and the equal volume of isopropyl alcohol was added. DNA pellet was washed in 70% ethanol. Dried DNA pellet was dissolved in 50 μl of TE buffer. 2 μl of the DNA was used in 20-50 μl of PCR mixture.

DNA preparation from nail samples. DNA from nail samples was extracted by the use of Red Extract-N-Amp Plant Kit (SIGMA). Examined nails were placed into a 2 ml Eppendorf tube, 100 μl of extraction buffer was added. After 10 min incubation at 95° C., 100 μl of dilution buffer was added. After vortex-mixing this DNA containing solution was ready for PCR.

Figure 2:
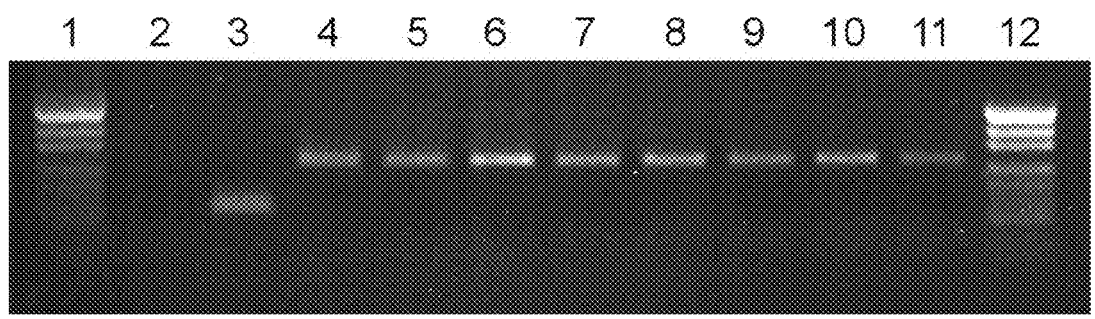
FIG. 2: Example of *Trichopyton rubrum* specific (lane 3) and pan-dermatophyte PCR products (lanes 4-11) analysis. Lanes: 1—molecular weight marker (fragment sizes (bp): 501, 489, 404, 331, 242, 190, 147, 111, 110, . . . ), 2—result of *Trichopyton rubrum* specific PCR performed for *Trichophyton mentagrophytes* DNA, 3—result of *Trichopyton rubrum* specific PCR performed for *Trichophyton rubrum* DNA (202 bp), lanes 4-11—results of pan-dermatophyte PCR performed for: *Microsporum audouinii* (lane 4), *Trichophyton mentagrophytes* var. *mentagrophytes* (lane 5), *Trichophyton schoenleninii* (lane 6), *Trichophyton terrestre* (lane 7), *Trichophyton rubrum* (lane 8), *Trichophyton tonsurans* (lane 9), *Trichophyton soudanese* (lane 10), *Epidermophyton floccosum* (lane 11).

Pan-dermatophyte PCR. 12 dermatophyte reference strains, 89 clinical dermatophyte isolates, 22 non-dermatophyte fungal isolates and purified human DNA (Table 2) were tested. PCR mixtures consisted of 10 μl of PCR Ready Mix (SIGMA), 0.2 μM concentration of both primers (panDerm1 and panDerm2) and 4 μl of DNA in a volume of 20 μl. PCR was performed in a MWG-Biotech thermal cycler. The time-temperature profile of PCR was 45 cycles of 30 s at 94° C., 30 s at 55° C., 30 s at 72° C., preceding by initial denaturation 10 min at 95° C. Presence of specific PCR products of approximately 366 bp was examined using electrophoresis on 2% agarose gel and staining with ethidium bromide (exemplary results presented on FIG. 2). The specificity of pan-dermatophyte PCR was confirmed. The specific 366 bp PCR product was detected for the reactions performed only for dermatophytes DNA.

*Trichophyton rubrum* specific PCR. The species and strains listed in Table 2 were tested. Each reaction was performed by the addition of 4 μl of the DNA from microorganisms listed in Table 2 and 0.2 mM of uni and Trubrum-rev to 10 μl of PCR Ready Mix (SIGMA). The amplification was performed in a thermal cycler (MWG-Biotech) and consisted of one initial cycle of denaturation for 5 min at 94° C. and 45 cycles of 30 s at 94° C., 30 s at 55° C. and 30 s of extension at 72° C. After the thermal cycles, the amplicons were electrophoresed in a 2% agarose gel and stained with ethidium bromide in order to check the presence of approximately 202 bp PCR products. To standardize the procedure, different DNA concentrations and thermal cycles were tested (data not shown). The specificity of *Trichophyton rubrum* PCR was confirmed. The specific 202 bp PCR product was detected for the reactions performed only for DNA extracted from *Trichophyton rubrum* strains (exemplary results presented on FIG. 2).

Figure 3:
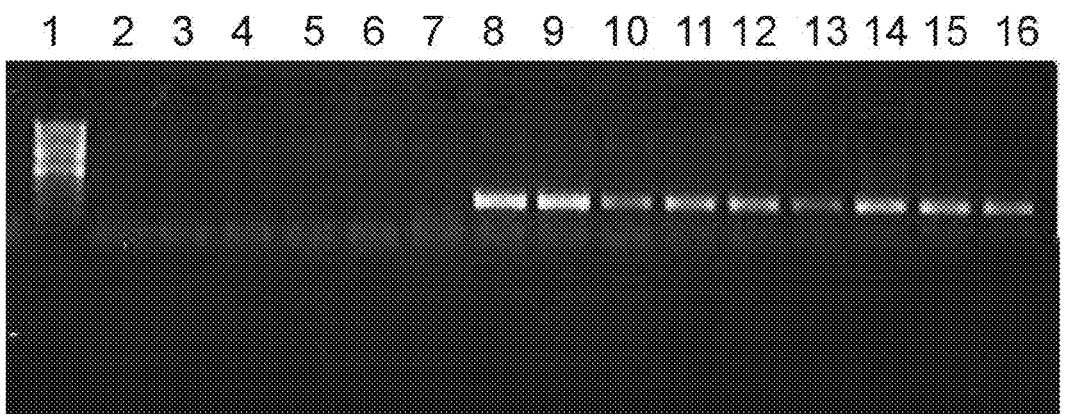
FIG. 3: Example of *Epidermophyton floccosum* specific PCR products analysis. (259 bp). Lanes: 1—molecular weight marker (100 bp DNA ladder, fragment sizes (bp): 2000, 1900, 1800, . . . , 100), 2—result for *Trichopyton rubrum*, 3—result for *Trichophyton tonsurans*, 4—result for *Trichophyton terrestre*, 5—result for *Trichophyton soudanese*, 6—result for *Candida albicans*, 7—result for *Sacharomyces cerevisiae*, lanes 8-16—results for *Epidermophyton floccosum* (different clinical isolates)

*Epidermophyton floccosum* specific PCR. The species and strains listed in Table 2 were tested. Each reaction was performed by the addition of 4 μl of the DNA from microorganisms listed above and 0.2 mM of each primer to 10 μl of PCR Ready Mix (SIGMA). The amplification was performed in a thermal cycler (MWG-Biotech) and consisted of one initial cycle of denaturation for 5 min at 94° C. and 45 cycles of 30 s at 94° C., 30 s at 55° C. and 30 s of extension at 72° C. After the thermal cycles, the amplicons were electrophoresed in a 2% agarose gel and stained with ethidium bromide in order to check the presence of approximately 259 bp PCR products (exemplary results presented on FIG. 3). To standardize the procedure, different DNA concentrations and thermal cycles were tested (data not shown). The specificity of *Epidermophyton floccosum*-PCR was confirmed as only the 14 fungi identified as *Epidermophyton floccosum* by classical examination were detected by the *Epidermophyton floccosum* specific PCR with uni and Ef-rev primers while the other dermatophytes, yeasts and moulds tested (table 2) were PCR negative.

Figure 4:
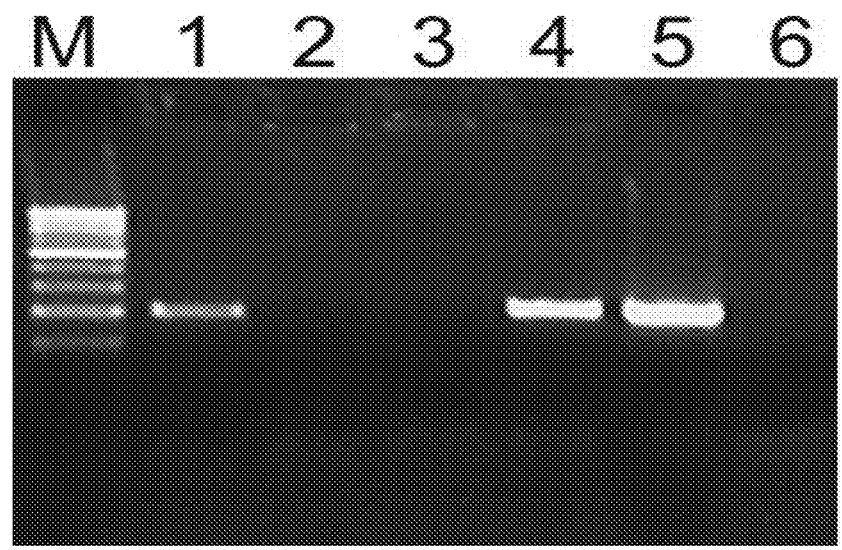
FIG. 4: Example of *Microsporum canis* specific PCR products analysis. (520 bp). Lanes: M—molecular weight marker (100 bp DNA ladder, fragment sizes (bp): 2000, 1900, 1800, . . . , 100), 1—result for *Microsporum canis*, 2—result for *Microsporum nana*, 3—result for *Microsporum audouinii*, 4—result for *Microsporum canis*, 5—result for *Microsporum canis*, 6—result for *Microsporum gypseum*.

*Microsporum canis* specific PCR The species and strains listed in Table 2 were tested. Each reaction was performed by the addition of 4 μl of the DNA from microorganisms listed above and 0.2 mM of each primer to 10 μl of PCR Ready Mix (SIGMA). The amplification was performed in a thermal cycler (MWG-Biotech) and consisted of one initial cycle of denaturation for 5 min at 94° C. and 45 cycles of 30 s at 94° C., 30 s at 65° C. and 30 s of extension at 72° C. After the thermal cycles, the amplicons were electrophoresed in a 2% agarose gel and stained with ethidium bromide in order to check the presence of approximately 259 bp PCR products (exemplary results presented on FIG. 4). To standardize the procedure, different DNA concentrations and thermal cycles were tested (data not shown). The specificity of *Microsporum canis*-PCR was confirmed as only the 10 fungi identified as *Microsporum canis* by classical examination were detected by the *Microsporum canis* specific PCR with Mc-for and Mc-rev primers while the other dermatophytes, yeasts and moulds tested (table 2) were PCR negative.

Figure 5:
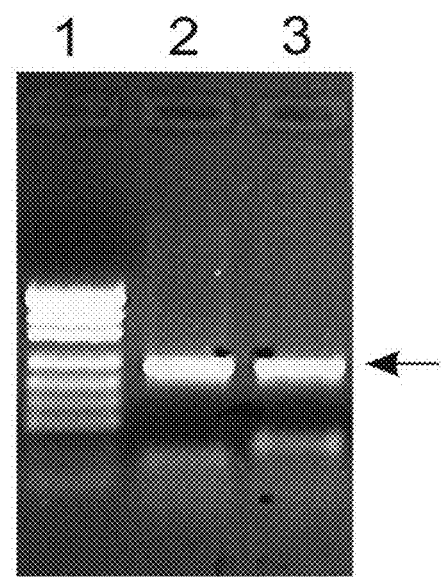
FIG. 5: Example of *Trichophyton mentagrophytes-Trichophyton tonsurans* complex specific PCR products analysis. (129 bp). Lanes: 1—molecular weight marker (511, 400, 350, 180, 111, 100, 80 bp), 2—result for *Trichophyton mentagrophytes*, 3—result for *Trichophyton tonsurans*

*Trichophyton mentagrophytes-Trichophyton tonsurans* complex specific PCR. The species and strains listed in Table 2 were tested. Each reaction was performed by the addition of 4 μl of the DNA from microorganisms listed above and 0.2 mM of each primer to 10 μl of PCR Ready Mix (SIGMA). The amplification was performed in a thermal cycler (MWG-Biotech) and consisted of one initial cycle of denaturation for 5 min at 94° C. and 45 cycles of 30 s at 94° C., 30 s at 65° C. and 30 s of extension at 72° C. After the thermal cycles, the amplicons were electrophoresed in a 2% agarose gel and stained with ethidium bromide in order to check the presence of approximately 129 bp PCR products (exemplary results presented on FIG. 5). To standardize the procedure, different DNA concentrations and thermal cycles were tested (data not shown). The specificity *Trichophyton mentagrophytes-Trichophyton tonsurans* complex-PCR was confirmed as only the 18 fungi identified as *Trichophyton mentagrophytes* or *Trichophyton tonsurans* by classical examination were detected by the *Trichophyton mentagrophytes-Trichophyton tonsurans* complex specific PCR with TmTt-for and TmTt-rev primers while the other dermatophytes, yeasts and moulds tested (table 2) were PCR negative.

Multiplex PCR. The multiplex PCR was performed using the two specific sets of primers described above: panDerm1+panDerm2 primers and uni+Trubrum-rev primers. The reaction was performed at various conditions. Different concentration combinations of primers were used: 0.2 mM of each primer or 0.2 mM of primers uni and Trubrum-rev together with 0.4 mM of primers panDerm1 and panDerm2. The following time-thermal profile was chosen: one initial cycle of denaturation for 5 min at 94° C. and 45 cycles of 30 s at 94° C., 30 s at 55° C. and 30 s of extension at 72° C. After the thermal cycles the amplicons were electrophoresed in a 2% agarose gel and stained with ethidium bromide.

Figure 6:
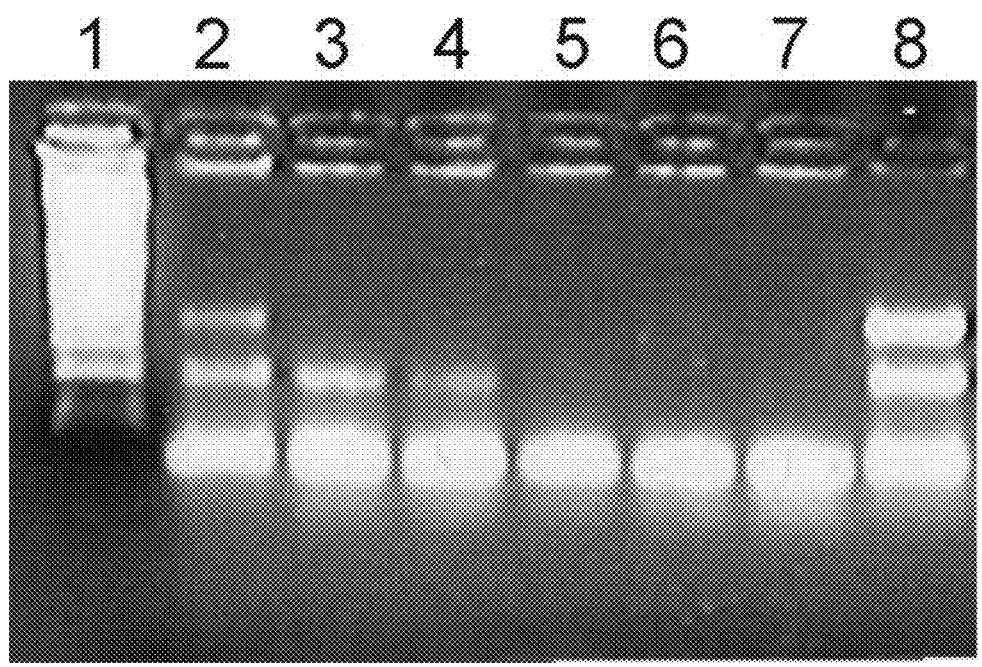
FIG. 6: Example of multiplex PCR and *Trichopyton rubrum* specific PCR products analysis. Lanes: 1—molecular weight marker (100 bp DNA ladder, fragment sizes (bp): 2000, 1900, 1800, . . . , 100), 2—result of multiplex PCR (pandermatophytes and *Trichopyton rubrum* specific PCR) performed for *Trichophyton rubrum* DNA, 3-4—result of *Trichopyton rubrum* specific PCR performed for *Trichophyton rubrum* DNA (202 bp), lanes 5-8—result of multiplex PCR (pandermatophytes and *Trichopyton rubrum* specific PCR) performed for: human (lane 5), *Sacharomyces cerevisiae* (lane 6), *Candida albicans* (lane 7), *Trichophyton rubrum* (lane 8)

Specificity of multiplex PCR was tested on DNA from all of the organisms listed in Table 1 and on human DNA (exemplary results are presented in FIG. 6). To further standardize the procedure, different DNA concentrations and thermal cycles were tested (data not shown). The multiplex PCR (and separately pan-dermatophyte PCR and *T. rubrum* specific) were examined on 92 clinical nail specimens.

Figure 7:
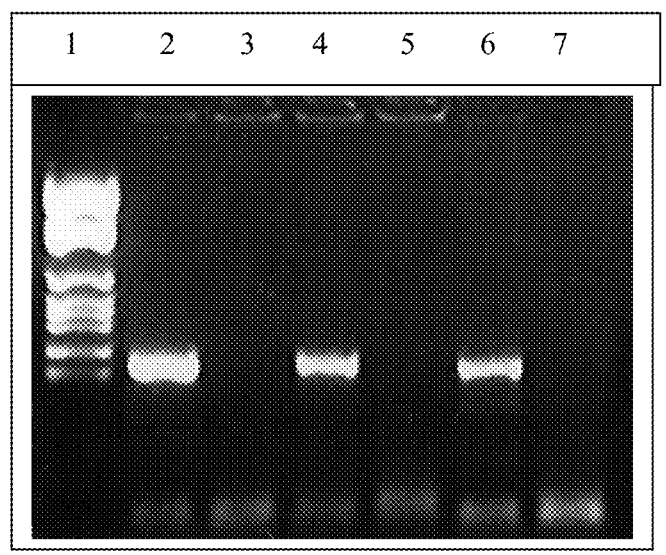
FIG. 7: Example of genus *Microsporum* specific PCR product analysis (115 bp) Lanes: 1—molecular weight marker (511, 400, 350, 180, 111, 100, 80 bp), 2—results for *Microsporum canis*, 3—results for *Trichopyton rubrum*, 4—results for *Microsporum gypseum*, 5—result for *Trichophyton tonsurans* 6—result for *Microsporum audouinii*, 7—result for *Trichophyton mentagrophytes* var. *interdigitale*.

Genus *Microsporum* specific PCR. The species and strains listed in Table 2 were tested. Each reaction was performed by the addition of 4 µl of the DNA from microorganisms listed above and 0.2 mM of each primer to 10 µl of PCR Ready Mix (SIGMA). The amplification was performed in a thermal cycler (MWG-Biotech) and consisted of one initial cycle of denaturation for 5 min at 94° C. and 45 cycles of 30 s at 94° C., 30 s at 65° C. and 30 s of extension at 72° C. After the thermal cycles, the amplicons were electrophoresed in a 2% agarose gel and stained with ethidium bromide in order to check the presence of approximately 115 bp PCR products (exemplary results presented on FIG. 7). To standardize the procedure, different DNA concentrations and thermal cycles were tested (data not shown). The specificity of *Microsporum canis*-PCR was confirmed as only the 18 fungi identified as *Microsporum canis* by classical examination were detected by the genus *Microsporum* specific PCR with Micr773-for and Micr885-rev primers while the other dermatophytes, yeasts and moulds tested (table 2) were PCR negative.

Figure 8:
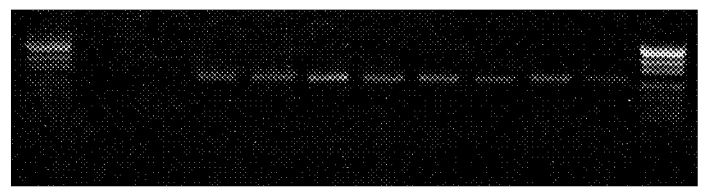
FIG. 8: Example of genus *Trichophyton* specific PCR product analysis (258 bp) Lanes: 1—molecular weight marker (511, 400, 350, 180, 111, 100, 80 bp), 2—result for *Microsporum canis*, 3—result for *Epidermophyton floccosum*, 4—result for *Trichopyton rubrum*, 5—result for *Trichophyton mentagrophytes* var. *interdigitale*, 6—result for *Trichophyton tonsurans*, 7—result for *Trichophyton violaceum*, 8—result for *Trichophyton soudanese*, 9—result for *Trichophyton schoenleninii*, 10—result for *Trichophyton terrestre*, 11—result for *Trichophyton mentagrophytes* var. *mentagrophytes*, 12—molecular weight marker (511, 400, 350, 180, 111, 100, 80 bp)

Genus *Trichophyton* specific PCR. The species and strains listed in Table 2 were tested. Each reaction was performed by the addition of 4 µl of the DNA from microorganisms listed in Table 2 and 0.2 mM of Trichopyros-for and Trichopyros-rev to 10 µl of PCR Ready Mix (SIGMA). The amplification was performed in a thermal cycler (MWG-Biotech) and consisted of one initial cycle of denaturation for 5 min at 94° C. and 45 cycles of 30 s at 94° C., 30 s at 60° C. and 30 s of extension at 72° C. After the thermal cycles, the amplicons were electrophoresed in a 2% agarose gel and stained with ethidium bromide in order to check the presence of approximately 258 bp PCR products. To standardize the procedure, different DNA concentrations and thermal cycles were tested (data not shown). The specificity of *Trichophyton rubrum* PCR was confirmed. The specific 258 bp PCR product was detected for the reactions performed only for DNA extracted from species belonging to genus *Trichophyton* (exemplary results presented on FIG. 8).

Figure 1:
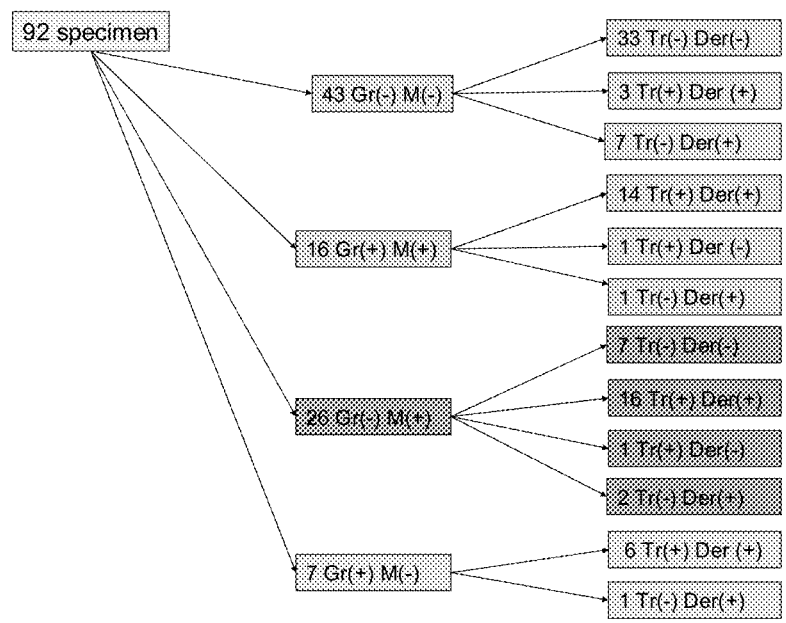
FIG. 1: The results of the specificity test of pan-dermatophyte and *Trichophyton rubrum* specific oligonucleotides performed on the group of 92 clinical isolates. Twenty-three were diagnosed as a *Trichophyton rubrum* positive, 26 were positive in direct microscopy, but culture-negative and 43 negative by classical examination. Gr: the result of culture observation; M: the result of microscopy; Tr: result of *Trichophyton rubrum* specific PCR; Der: result of pandermatophyte PCR; (−)—negative; (+)—positive

Results: The results of the pan-dermatophyte PCR, the *Trichochyton rubrum* specific PCR, *Microsporum canis* specific PCR, *Trichophyton mentagrophytes-Trichophyton tonsurans* complex specific PCR, the *Epidermophyton floccosum* specific PCR, genus *Microsporum* specific PCR and genus *Trichophyton* specific PCR are compared to the results obtained by classical diagnostic procedures (microscopy and culture). Exemplary juxtaposition of the results are presented in FIG. 1. In the majority of the cases the classical and PCR results were in agreement. However, in 10/43 microscopy and culture negative samples PCR detected dermatophyte DNA of which 3 were also *T. rubrum* PCR positive and in 7 of 26 microscopy but culture negative samples no dermatophyte DNA was detected. The discrepancy between the classical and PCR diagnosis in these cases could arise due to:
- the presence of only few (below the detection level by microscopy) and non-viable dermatophyte cells in the specimen,
- contamination of the culture by fast-grow species present in the environment (e.g. *Alternaria*) (when negative by culture and positive by microscopy)
- misdiagnosis of the species (direct microscopy) because of relatively low sensitivity shows false negative results in up to 15% cases [2].

Example 3

DNA Extraction Method—the Protocol for Invented DNA Extraction Method from Dermatophyte Infected Nails Sixty-four nail samples were randomly chosen from samples received at the Laboratory of Mycology at SSI for microscopy and culture of dermatophytes and *Candida* (Table 3). Fourteen were diagnosed as *T. rubrum*, two as *T. mentagrophytes*, one as a *T. tonsurans*, two as *Aspergillus* sp., two as *Candida* sp., one as *Alternaria* sp., three as *Acremonium* sp. and 39 were found negative.

TABLE 3

Microorganisms used in the study

| Specimen diagnosed by routine Mycology Lab as | Number of clinical isolates |
| --- | --- |
| *Trichophyton rubrum* | 14 |
| *Trichophyton mentagrophytes* | 2 |
| *Aspergillus* sp. | 2 |
| *Candida* sp. | 2 |
| *Acremonium* sp. | 3 |
| *Alternaria* | 1 |
| *Trichophyton tonsurans* | 1 |
| Negatives (no growth of any fungi) | 39 |

DNA from 64 clinical specimens listed in table 3 were extracted according to the following protocol:
1. The nails were placed in 2 ml Eppendorf tubes
2. 100 µl (can be increased up to 500) lysis buffer L1 (250 mM KCl, 60 mM NaHCO$_3$, 50 mM Tris-HCl [pH 9.5]) was added
3. The tubes were incubated 10 min in 95° C.
4. 100 µl (can be increased up to 500) neutralizing buffer L2 (2% BSA in water) was added (note that the volumes of lysis buffer L1 and neutralizing buffer L2 have to be equal)
5. The tubes were vortex-mixed.

Multiplex PCR. Each reaction was performed by the addition of 4 µl of the DNA from microorganisms listed above and 0.2 mM of each primer (uni, Trubrum-rev, panDerm1 and panDerm2) to 10 µl of PCR Ready Mix (SIGMA) and to 5.2 µl DNase, Rnase free water. The amplification was performed in a thermal cycler (MWG-Biotech) and consisted of one initial cycle of denaturation for 5 min at 94° C. and 45 cycles of 30 s at 94° C., 30 s at 55° C. and 30 s of extension at 72° C. After the thermal cycles, the amplicons were electrophoresed in a 2% agarose gel and stained with ethidium bromide Results. 36 of 39 culture-negative patient samples examined were negative also by the multiplex PCR described above and in three *Trichophyton rubrum* DNA were detected. All of the samples diagnosed as *Trichophyton rubrum* positive by classical examination were also positive according to multiplex PCR. Three of dermatophytes that were non-*rubrum Trichophyton* species (one *Trichophyton tonsurans* and two *Trichophyton mentagrophytes*) by classical evaluation were diagnosed as pan-dermatophyte positive, *Trichophyton rubrum* negative by multiplex PCR. One of three specimens diagnosed as *Acremonium* sp. by classical examination was diagnosed as *Trichophyton rubrum* bp PCR. The discrepancy between the classical and PCR diagnosis could arise due to the reasons listed in the results of Example 2.

Example 4

DNA Extraction Method—Application for DNA from Yeasts

Material and Methods.

Strains. Thirty-eight different *Candida* strains and one *Sacaromyces cerevisiae* were chosen from the collection of Laboratory of Mycology at SSI. *Pichia pastoris* strain X-33 was from Invitrogen.

DNA preparation from *Candida* cultures. DNA from the cultured *Candida* strains was extracted by the use of Red Extract-N-Amp Plant Kit (SIGMA). The fungal colonies were placed into a 2 ml Eppendorf tube, 100 μl of extraction buffer was added. After 10 min incubation at 95° C., 100 μl of dilution buffer was added. After vortex-mixing this DNA containing solution was ready for PCR.

DNA preparation from *Pichia pastoris* and *Saccharomyces cerevisiae* cultures. DNA from one *Pichia pastoris* and one from *Saccharomyces cerevisiae* strain were extracted according to the following protocol:
1. The piece of mycelia was placed in 2 ml Eppendorf tubes
2. 100 μl lysis buffer L1 (250 mM KCl, 60 mM NaHCO$_3$, 50 mM Tris-HCl [pH 9.5]) was added
3. The tubes were incubated 10 min in 95° C.
4. 100 μl neutralizing buffer L2 (2% BSA in water) was added
5. The tubes were vortex-mixed.

*Candida albicans* PCR. Thirty-eight strains were tested. Each reaction was performed by the addition of 4 μl of the DNA and 0.2 mM of AAT1a478 for and AAT1a478 rev described elsewhere (17) to 10 μl of PCR Ready Mix (SIGMA). The amplification was performed in a thermal cycler (MWG-Biotech) and consisted of one initial cycle of denaturation for 5 min at 95° C. and 45 cycles of 30 s at 94° C., 30 s at 60° C. and 30 s of extension at 72° C. After the thermal cycles, the amplicons were electrophoresed in a 2% agarose gel and stained with ethidium bromide in order to check the presence of approximately 478 bp PCR products.

Figure 9:
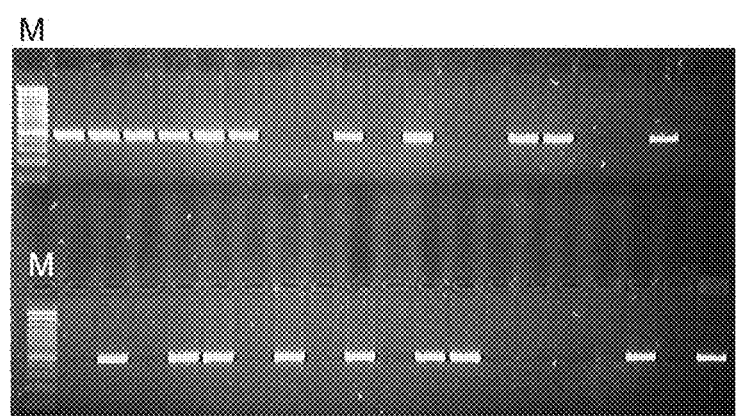
FIG. 9: Example of *Candida albicans* AAT1a gene amplification (478 bp)

Results. Twenty obtained PCR products were sequenced (MWG-Biotech, De) confirming the presence of 20 *Candida albicans* strains (exemplary results are presented in FIG. 9)

*Candida glabrata* PCR. Thirty-eight strains were tested. Each reaction was performed by the addition of 4 μl of the DNA and 0.2 mM of TRP1F1 for and TRP1R1rev described elsewhere (18) to 10 μl of PCR Ready Mix (SIGMA). The amplification was performed in a thermal cycler (MWG-Biotech) and consisted of one initial cycle of denaturation for 5 min at 95° C. and 45 cycles of 30 s at 94° C., 30 s at 60° C. and 1.5 min of extension at 72° C. After the thermal cycles, the amplicons were electrophoresed in a 2% agarose gel and stained with ethidium bromide in order to check the presence of approximately 820 bp PCR products.

Results. Seven obtained PCR products were sequenced (MWG-Biotech, De) confirming the presence of 7 *Candida glabrata* strains (exemplary results are presented in FIG. 10).

*Sacharomyces cerevisiae* PCR. The reaction was performed by the addition of 4 μl of the DNA and 0.2 mM of ScMTG-for (5' AGGTCTATTCGTATTGGTATCCAAGC 3') (SEQ ID NO: 14) and ScMTG-rev (5' CCAGTAAGT-TCCTTCATCAGACA 3') (SEQ ID NO: 15) to 10 μl of PCR Ready Mix (SIGMA). The amplification was performed in a thermal cycler (MWG-Biotech) and consisted of one initial cycle of denaturation for 5 min at 95° C. and 45 cycles of 30 s at 94° C., 30 s at 56° C. and 2 min of extension at 72° C. After the thermal cycles, the amplicons were electrophoresed in a 1% agarose gel and stained with ethidium bromide in order to check the presence of approximately 1440 bp PCR products.

Results The specific PCR product was sequenced and confirmed the amplification of the fragment of maltriose transporter gene from *Saccharomyces cerevisiae* (result presented on FIG. 11)

*Pichia pastoris* PCR. The reaction was performed by the addition of 4 μl of the DNA and 0.2 mM of serc16-for (5' CGGATCAATTATGGTGACGAGTAGG 3') (SEQ ID NO: 16) and sec16-rev (5' AGGAACAGTTTGTGGGT-TCAAATCAGG 3') (SEQ ID NO: 17) to 10 μl of PCR Ready Mix (SIGMA). The amplification was performed in a thermal cycler (MWG-Biotech) and consisted of one initial cycle of denaturation for 5 min at 95° C. and 45 cycles of 30 s at 94° C., 30 s at 50° C. and 30 s of extension at 72° C. After the thermal cycles, the amplicons were electrophoresed in a 1% agarose gel and stained with ethidium bromide in order to check the presence of approximately 2879 bp PCR products. Results: The specific PCR product was sequenced and confirmed the amplification of the fragment of sec16 gene from *Pichia pastoris* (result presented on FIG. 11).

Example 4

Detection of Amplification Products from Example 2, 3 and 4

The detection of the dermatophyte or *Trichophyton rubrum*, or *Epidermophyton floccosum*, or *Trichophyton mentagrophytes-Trichophyton tonsurans* complex, or *Microsporum canis*, or *Candida albicans*, or *Candida glabrata* specific DNA segments is carried out by ethidium bromide staining of the specific bands in a 2% agarose gel. The exemplary electrophorogram is presented in FIG. 2. The detection of the *Pichia pastoris*, or *Saccharomyces cerevisiae* DNA segments is carried out by ethidium bromide staining of the specific bands in a 1% agarose gel. The electrophorogram is presented in FIG. 11.

REFERENCES

1. Hainer, B. L. (2003) Dermatophyte infections. *Am. Fam. Physician* 67, 101-108.
2. Rippon, J. W. (1988) *Medical mycology: the pathogenic fungi and the pathogenic actinomycetes*. Philadelphia.
3. Kanbe, T., Y. Suzuki, A. Kamiya, T. Mochizuki, M. Fujihiro, and A. Kikuchi (2003) PCR-based identification of common dermatophyte species using primer sets specific for the DNA topoisomerase II genes. *J. Dermatol. Sci.* 32, 151-161.
4. Liu, D., S. Coloe, R. Baird, and J. Pedersen (2000) Application of PCR to the identification of dermatophyte fungi. *J. Med. Microbiol.* 49, 493-497
5. Faggi, E., G. Pini, and E. Campisi (2002) PCR fingerprinting for identification of common species of dermatophytes. *J. Clin. Microbiol.* 40, 4804-4805.
6. Kano, R., Y. Nakamura, S. Watanabe, H. Takahashi, H. Tsujimoto, and A. Hasegawa (1998) Differentiation of

*Microsporum* species by random amplification of polymorphic DNA (RAPD) and southern hybridization analyses. *Mycoses* 41, 229-233.
7. Shin, J. H., J. H. Sung, S. J. Park, J. A. Kim, J. H. Lee, D. Y. Lee, E. S. Lee, and J. M. Yang (2003) Species identification and strain differentiation of dermatophyte fungi using polymerase chain reaction amplification and restriction enzyme analysis. *J. Am. Acad. Dermatol.* 48, 857-865.
8. Liu D, Coloe S, Baird R, Pedersen J. (1997) Molecular determination of dermatophyte fungi using the arbitrarily primed polymerase chain reaction. *Br J Dermatol.* 137(3), 351-5.
9. Ninet B, Jan I, Bontems O, Lechenne B, Jousson O, Panizzon R, Lew D, Monod M. (2003) Identification of dermatophyte species by 28S ribosomal DNA sequencing with a commercial kit *J Clin Microbiol.* 41(2):826-30
10. Liu D, Coloe S, Baird R, Pederson J. Rapid minipreparation of fungal DNA for PCR. (2000) *J. Clin. Microbiol.* 38(1):471
11. Gaedigk A, Gaedigk R, Abdel-Rahman S M. Genetic Heterogeneity in the rRNA Gene Locus of *Trichophyton tonsurans*. (2003) *J. Clin. Microbiol.* 41(12):5478-87.
12. Kano R, Hirai A, Muramatsu M, Watari T, Hasegawa A. (2003) Direct detection of dermatophytes in skin samples based on sequences of the chitin synthase 1 (CHS1) gene *J Vet Med Sci.* 65(2):267-70
13. Kano R, Aihara S, Nakamura Y, Watanabe S, Hasegawa A. (2001) Chitin synthase 1 (Chs1) gene sequences of *Microsporum equinum* and *Trichophyton equinum Vet. Microbiol.* 78(1):85-90
14. Kano R, Nakamura Y, Watanabe S, Hasegawa A. (2000) Detection of *Microsporum canis* in the skin scrapings and hairs of dogs with dermatophytosis based on sequences of the chitin synthase 1 gene *Microbiol. Immunol.* 44(7): 605-7
15. Machouart-Dubach M, Lacroix C, de Chauvin M F, Le Gall I, Giudicelli C, Lorenzo F, Derouin F. (2001) Rapid discrimination among dermatophytes, *Scytalidium* spp., and other fungi with a PCR-restriction fragment length polymorphism ribotyping method. J Clin Microbiol. February; 39(2):685-90.
16. Ninet B, Jan I, Bontems O, Lechenne B, Jousson O, Panizzon R, Lew D, Monod M. (2003) Identification of dermatophyte species by 28S ribosomal DNA sequencing with a commercial kit. J Clin Microbiol. February; 41(2): 826-30.
17. Tavanti A., Gow N. A. R., Senesi S., Maiden M. C. J., Odds F. C. (2003) Optimization and validation of multilocus sequence typing for *Candida albicans* J. Clin. Microbiol. August: 41(8):3765-3776
18. Dodgson A. R., Pujol C., Denning D. W., Soll D. R., Fox A. J. (2003) Multilocus sequence typing of *Candida glabrata* reveals geographically enriched clades J. Clin. Microbiol. December: 41(12):5709-5717

The invention claimed is:

1. A method of extracting nucleic acid from fungi comprising the following steps:
   (a) heating a patient sample containing the fungi in a lysis buffer to between 80 and 100° C. for a period not to exceed 10 minutes, said patient sample selected from the group consisting of hair, skin, and nail; and
   (b) mixing the solution with a neutralizing buffer;
   wherein said lysis buffer consists of, in aqueous solution:
   (i) a reducer selected from the group consisting of sodium carbonate, sodium sulfate, beta-mercaptoethanol, dithiothreitol, sodium sulfide, sodium chloride, sodium chlorite, sodium iodate, and sodium bicarbonate; (ii) a salt selected from the group consisting of potassium chloride and ammonium persulfate; and (iii) a buffering compound selected from the group consisting of CAPSO, TRIS, HEPES, and phosphate buffer;
   wherein said neutralizing buffer is an aqueous 0.5-3% w/v protein solution; and
   wherein the cell wall of said fungi is not disrupted prior to step (a).

2. The method according to claim 1, wherein said fungi is a species belonging to the genera *Trichophyton, Epidermophyton*, or *Microsporum*, or a yeast.

3. The method according to claim 1, wherein said lysis buffer consists of sodium bicarbonate, potassium chloride, and TRIS.

4. The method according to claim 1, wherein said patient sample in step (a) is heated to 95° C. for 10 minutes.

5. The method according to claim 1, wherein the neutralizing buffer is an aqueous 2% w/v protein solution.

6. The method according to claim 1, wherein the protein in said neutralizing buffer is BSA or ovalbumin.

7. A method of detecting fungi infections in patient samples comprising the following steps:
   (A) extracting nucleic acid from fungi by the method according to claim 1;
   (B) amplifying the nucleic acid with PCR using fungus-specific primers; and
   (C) detecting fungus-specific genes.

8. The method according to claim 7, wherein said fungus-specific primers are selected from the group consisting of panDerm1 (SEQ ID NO: 1), panDerm2 (SEQ ID NO: 2), uni (SEQ ID NO: 3), Trubrum-rev (SEQ ID NO: 4), Ef-rev (SEQ ID NO: 5), Micr773-for (SEQ ID NO: 10), Micr885-rev (SEQ ID NO: 11), Trichopyros-for (SEQ ID NO: 12); and Trichopyros-rev (SEQ ID NO: 13).

9. The method according to claim 1, wherein said heating in step (a) is for 10 minutes.

10. The method according to claim 7, wherein said heating in step (a) is for 10 minutes.

* * * * *